United States Patent [19]

Kozikowski et al.

[11] Patent Number: 5,227,508
[45] Date of Patent: Jul. 13, 1993

[54] 3-DEOXY-3-SUBSTITUTED ANALOGS OF PHOSPHATIDYLINOSITOL

[75] Inventors: Alan P. Kozikowski, Ponte Verde Beach; Werner Tuckmantel; Abdul H. Faug, both of Jacksonville, all of Fla.; Garth Powis, Tucson, Ariz.

[73] Assignee: Mayo Foundation for Medical Education and Research, Rochester, Minn.

[21] Appl. No.: 825,523

[22] Filed: Jan. 24, 1992

[51] Int. Cl.$^5$ ............................................. C07F 9/10
[52] U.S. Cl. ......................................... 558/155; 558/180
[58] Field of Search ................................... 558/155, 180

[56] References Cited

U.S. PATENT DOCUMENTS

| 4,515,722 | 5/1985 | Yang et al. | 260/403 |
| 4,988,682 | 1/1991 | Kozikowski | 514/150 |
| 5,053,399 | 10/1991 | Kozikowski | 514/150 |

OTHER PUBLICATIONS

Martin, T. W. et al. *J. Biol. Chem.* 1987, 262(27), 13086–13092.
Kuksis, A. et al. *Lipids* 1989, 24(5), 396–407.
G. Powis et al., *Cancer Chemother. Pharmacol.*, 29, 95 (Dec. 1991).
U. Kikkawa et al., *Ann. Rev. Cell Biol.*, 2, 149 (1986).
M. Whitman et al., *Biochim. Biophys. Acta*, 948, 327 (1988).
R. F. Irvine et al., *Nature*, 320, 631 (1986).
Y. Nishizuka, *Science*, 225, 1365 (1984).
Y. Sugimoto et al., *Molec. Cellular Biol.*, 5, 3194 (1985).
K. Fukami et al., *PNAS USA*, 85, 9057 (1988).
S. K. Fisher et al., *J. Neurochem.*, 48, 999 (1987).
Y. Fukui, *Oncogene Res.*, 4, 283 (1989).

*Primary Examiner*—Robert W. Ramsuer
*Assistant Examiner*—Michael G. Ambrose
*Attorney, Agent, or Firm*—Merchant, Gould, Smith, Edell, Welter & Schmidt

[57] ABSTRACT

The invention provides 3-deoxy-3-substituted analogs of phosphatidylinositol which are useful to inhibit the growth of mammalian cells, i.e., to treat neoplastic conditions and other proliferative disorders of mammalian cells.

15 Claims, 6 Drawing Sheets

3-DEOXY-3-SUBSTITUTED ANALOGS OF PHOSPHATIDYLINOSITOL

BACKGROUND OF THE INVENTION

For mammalian cells to survive, they must be able to respond rapidly to changes in their environment. Furthermore, for cells to reproduce and carry out other cooperative functions, they must be able to communicate efficiently with each other. Cells most frequently adapt to their environment and communicate with one another by means of chemical signals. An important feature of these signaling mechanisms is that in almost all cases a cell is able to detect a chemical signal without it being necessary for the chemical messenger itself to enter the cell. This permits the cell to maintain the homeostasis of its internal environment, thereby permitting the cell to respond to its external environment without being adversely effected by it.

These sensing functions are carried out by a variety of receptors, which are dispersed on the outer surface of the cell and function as molecular antennae. These receptors detect an incoming messenger and activate a signal pathway that ultimately regulates a cellular process such as secretion, contraction, metabolism or growth. In the cell's cellular plasma membrane, transduction mechanisms translate external signals into internal signals, which are then carried throughout the interior of the cell by chemicals known as "second messengers."

In molecular terms, the process depends on a series of proteins within the cellular plasma membrane, each of which transmits information by inducing a conformational change in the protein next in line. At some point, the information is assigned to small molecules or even to ions within the cell's cytoplasm, which serve as the above-mentioned second messengers. The diffusion of the second messengers enables a signal to propagate rapidly throughout the cell.

Several major signal pathways are now known, but two seem to be of primary importance. One employs cyclic nucleotides as second messengers. These cyclic nucleotides activate a number of proteins inside the cell, which then cause a specific cellular response. The other major pathway employs a combination of second messengers that includes calcium ions as well as two substances whose origin is remarkable: myo-inositol-1,4,5-trisphosphate ($IP_3$) and diacylglycerol (DG). These compounds are cannibalized from the plasma membrane itself, by enzymes which are activated by specific cellular membrane receptors. However, it should be noted that myo-inositol in its non-phosphorylated form first must be synthesized by the cell from glucose or be obtained from the extracellular environment. The structural formula of myo-inositol is shown below:

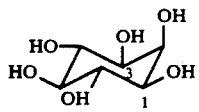

wherein the term "myo" refers to the stereochemical configuration of the inositol molecules. Since all known inositol second messengers use the D-myo-configuration of inositol, the term "inositol" will herein be understood to refer to D-myo-inositol. To form $IP_3$, a receptor molecule on the surface of the cellular plasma membrane transmits information through the cellular plasma membrane and into the cell by means of a family of G proteins, which are cellular plasma membrane proteins that cannot be active unless they bind to guanosine triphosphate (GTP). The G proteins activate the so-called "amplifier" enzyme phospholipase C, which is on the inner surface of the cellular plasma membrane. Phospholipase C cleaves the cellular plasma membrane lipid, phosphatidylinositol-4,5-bisphosphate ($PIP_2$) into DG and $IP_3$. $IP_3$ is a water-soluble molecule, and therefore, upon being released from the inner surface of the cellular plasma membrane, it rapidly diffuses into the cytoplasm. $IP_3$ then releases calcium ions ($Ca^{2+}$) from non-mitochondrial stores, to increase the cytoplasmic free $Ca^{2+}$ concentration. DG is an activator of protein kinase C. See U. Kikkawa et al., *Ann. Rev. Cell Biol.*, 2, 149 (1986). Taken together, the increase in cytoplasmic free $Ca^{2+}$ concentration and the increased activity of protein kinase C leads to a sequence of events that culminates in DNA synthesis and cell proliferation (See M. Whitman et al., *Biochim. Biophys. Acta*, 948, 327 (1988)). Other inositol phosphates, in addition to $IP_3$, are formed in the cell. For example, phosphorylation of $IP_3$ by a specific 3-kinase gives inositol-1,3,4,5-tetrakisphosphate ($IP_4$) (R. F. Irvine et al., *Nature*, 320, 631 (1986)), which may act synergistically with $IP_3$ in the activation of $Ca^{2+}$-mediated responses in several systems.

Recently, another phosphatidylinositol signalling pathway has been identified and linked to the action of some growth factors and oncogenes. Phosphatidylinositol-3'-kinase (also designated type 1 phosphatidylinositol kinase) is found associated with a number of protein tyrosine kinases including the ligand-activated receptors for insulin, platelet derived growth factor (PDGF), epidermal growth factor (EGF), and colony-stimulating factor-1 (CSF-1) as well as protooncogene and oncogene tyrosine kinases (Y. Fukui et al., *Oncogene Res.*, 4, 283 (1989)). This enzyme phosphorylates the D-3 position of the myo-inositol ring of phosphatidylinositols to give a class of phosphatidylinositol-3'-phosphates that are not substrates for hydrolysis by phosphatidylinositol phospholipase C and, therefore, appear to exert their signalling action independently of the inositol phosphate pathway.

Subsequently, DG and $IP_3$ are recycled. DG is recycled by a series of chemical reactions which constitute one component of the lipid cycle, and $IP_3$ is recycled by a series of reactions known as the phosphatidylinositol cycle. The two cycles converge at the point when inositol is chemically linked to DG. The DG-bound inositol is phosphorylated in a series of steps which ultimately results in the reformation of phosphatidylinositol diphosphate.

Previously, A. P. Kozikowski (U.S. Pat. No. 5,053,399) disclosed the synthesis of a number of D-3-deoxy-3-substituted-myo-inositols, in the expectation that these compounds would act as antimetabolites of myo-inositol-derived second messengers. In theory, such myo-inositol isosteres could act either by blocking the formation of certain phosphatidylinositols and inositol phosphates or by forming fraudulent analogs thereof. In fact, certain of these analogs, such as 3-deoxy-3-fluoro-myo-inositol, were found to exhibit cell growth inhibitory activities against normal NIH 3T3 cells in culture and several oncogene transformed NIH 3T3 cell lines. However, the D-3-deoxy-3-substituted-myo-inositol analogs were only effective inhibitors of cell growth in the absence of myo-inositol. In the presence of physiological concentrations of myo-inositol in the growth medium, the growth inhibitory effect of the analogs was antagonized. It is believed that myo-inositol effectively competes with the D-3-deoxy-3-substituted myo-inositol analogs either for uptake into the cell and/or for incorporation by the cell to phosphatidylinositols.

Therefore, a continuing need exists for analogs of phosphatidylinositol which are effective to inhibit the phosphatidylinositol cycle in a cell, e.g., to block cell growth, preferably to inhibit or prevent the growth of neoplastic cells and/or neoplastic transformation.

SUMMARY OF THE INVENTION

The present invention provides a bioactive 3-deoxy-3-substituted analogs of phosphatidylinositol of formula (I):

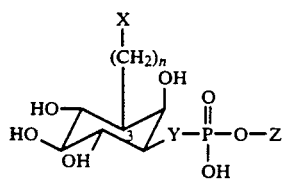

or a pharmaceutically acceptable salt thereof; wherein X is selected from the group consisting of halo (Cl, F, Br, I), azido ($N_3$), CN, NC, OR, SR, $N(R)_2$, $CO_2R$, C(O)R, $P(O)(OR)_2$, $CF_3$, S(O)R and $SO_2R$; wherein each R is H, ($C_1$-$C_{22}$)alkyl, preferably ($C_7$-$C_{20}$)alkyl (such as n-heptyl, n-deyl, isodecyl, n-pentadecyl, n-hexadecyl, n-octadecyl and n-eicosyl); ($C_6$-$C_{10}$)aryl, preferably phenyl or naphthyl; ($C_3$-$C_8$)cycloalkyl, preferably cyclohexyl or cyclopentyl; ($C_2$-$C_{22}$)alkenyl, preferably ($C_7$-$C_{20}$)alkenyl, wherein the alkenyl group comprises 1-3 double bonds; ($C_5$-$C_8$)cycloalkenyl, preferably cyclohexenyl and cyclopentenyl; ($C_7$-$C_{32}$)aralkyl, ($C_7$-$C_{32}$)alkylaryl, ($C_9$-$C_{32}$)aralkenyl and ($C_9$-$C_{32}$)alkenylaryl; and wherein the R groups are unsubstituted or are substituted by the group X wherein R is unsubstituted;

n is 0 or 1;
Y is O, S, NR, $CH_2$, $CF_2$, or CHF; and
Z is

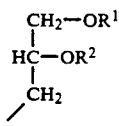

wherein $R^1$ and $R^2$ are individually R, C(O)R, $CO_2R$, C(O)NHR, C(O)SR or $P(O)(OR)_2$.

Preferably, X is halo, most preferably F; $N_3$, $NH_2$ or $P(O)(OR)_2$, wherein R is H; Y is $CH_2$, CHF or $CF_2$ and $R^1$ and $R^2$ are ($C_7$-$C_{22}$)alkanoyl or ($C_7$-$C_{22}$)alkenoyl groups, i.e., are the alkanoyl or alkenoyl residues of fatty acids such as those present in naturally occurring phosphatidylinositols. Representative examples of these substituted groups (XR—) are hydroxyethyl, 3-methoxypropyl, 4-hydroxyphenyl, 3- or 4-chlorobenzyl, 4-trifluorobenzyl, 2-aminophenethyl, 2-carboxyphenylethenyl, 4-cyanomethylphenyl, 4-(N,N-dimethylphenyl)cyclohexyl, 2,6-dimethoxyphenyl, 2-ethoxy-1-naphthyl, 4-amino-4-carboxybutyl, 1-naphthylmethyl, 1-(N-ethylaminophenyl)-n-butyl 1,2-carbamoylbenzyl, 4-sulfonylbenzyl, 4-sulfinylbenzyl, 2-methylthiophenyl, 2,4-dinitrobenzyl, 4-phenylbenzyl, 4-phenoxyphenethyl, and the like.

The present invention also provides a method for inhibiting cellular growth by inhibiting the phosphatidylinositol cycle in mammalian cells, including human cells, which comprises administering to said mammal an effective phosphatidylinositol cycle-inhibiting amount of a compound of formula I. Thus, a method is also provided wherein the compounds of formula I are used to treat phosphatidylinositol cycle-dependent conditions in mammals, including humans, which comprises administering to said mammal a phosphatidylinositol cycle-inhibiting amount of a compound of formula I, which is effective to cure or ameliorate said condition or the symptoms thereof.

Inositol phosphate cycle-dependent conditions include normal or abnormal cellular growth as found in cancers and in other neoplastic conditions, as well as biochemical processes relevant to arthritis, pain, inflammation, and platelet aggregation. See Y. Nishizuka, *Science*, 225, 1365-1370 (1984); S. K. Fisher et al., *J. Neurochem.*, 48, 999-1017 (1987); Y. Sugimoto et al., *Molecular and Cellular Biology*, 5, 3194-3198 (1985); and K. Fukami et al., *Proc. Natl. Acad. Sci., USA*, 85, 9057-9061 (1988). Solid tumors such as sarcomas, melanomas, carcinomas or lymphomas can be treated with the present compounds.

The improved bioactivity of the present compounds is believed to be due, in part, to their ability to resist antagonism by endogenous myo-inositol. For example, the compounds of formula I can inhibit the growth of normal NIH 3T3 cells and v-sis oncogene transformed NIH 3T3 cells and of HT-29 colon carcinoma cells in culture. The cell growth inhibition occurs at physiological concentrations of myo-inositol. Yang et al. (U.S. Pat. No. 4,515,722) generally disclose phospholipase C inhibitors of the structure (II):

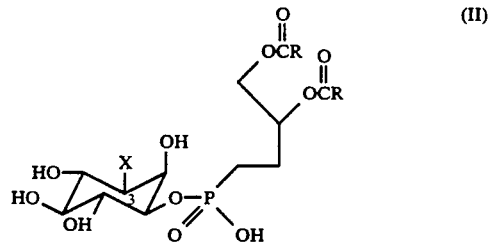

wherein X is OH (myo-inositol), and R is as defined as, for example, in Table I. At Col. 3, line 67 to Col. 4, line 2, it is also disclosed that inositol can be "substituted" with $N_3$, halo and alkyl. An example of a simple analog containing a modified inositol ring in the patent is 2-fluoro-2-deoxy-1-O-octadecylphosphonylscylloinositol (24) (Col. 18, lines 34-44). An example of a compound of formula II wherein X is OH is given as Example 8. A protected 3-deoxy-3-azido-myo-inositol is disclosed in Example 23, but was apparently not incorporated into a compound of formula II.

However, the compounds of formula I are O-(alkyloxyphosphonyl)-substituted inositols (or disubstituted phosphates), while the compounds of formula II are O-(alkylphosphonyl)inositols (or alkylphosphonates). Also, the Yang et al. patent does not disclose that the compounds disclosed therein have anticancer or antiproliferative activity, but rather, discloses that they are antiinflammatory agents or analgesics.

DETAILED DESCRIPTION OF THE INVENTION

Figure 1:
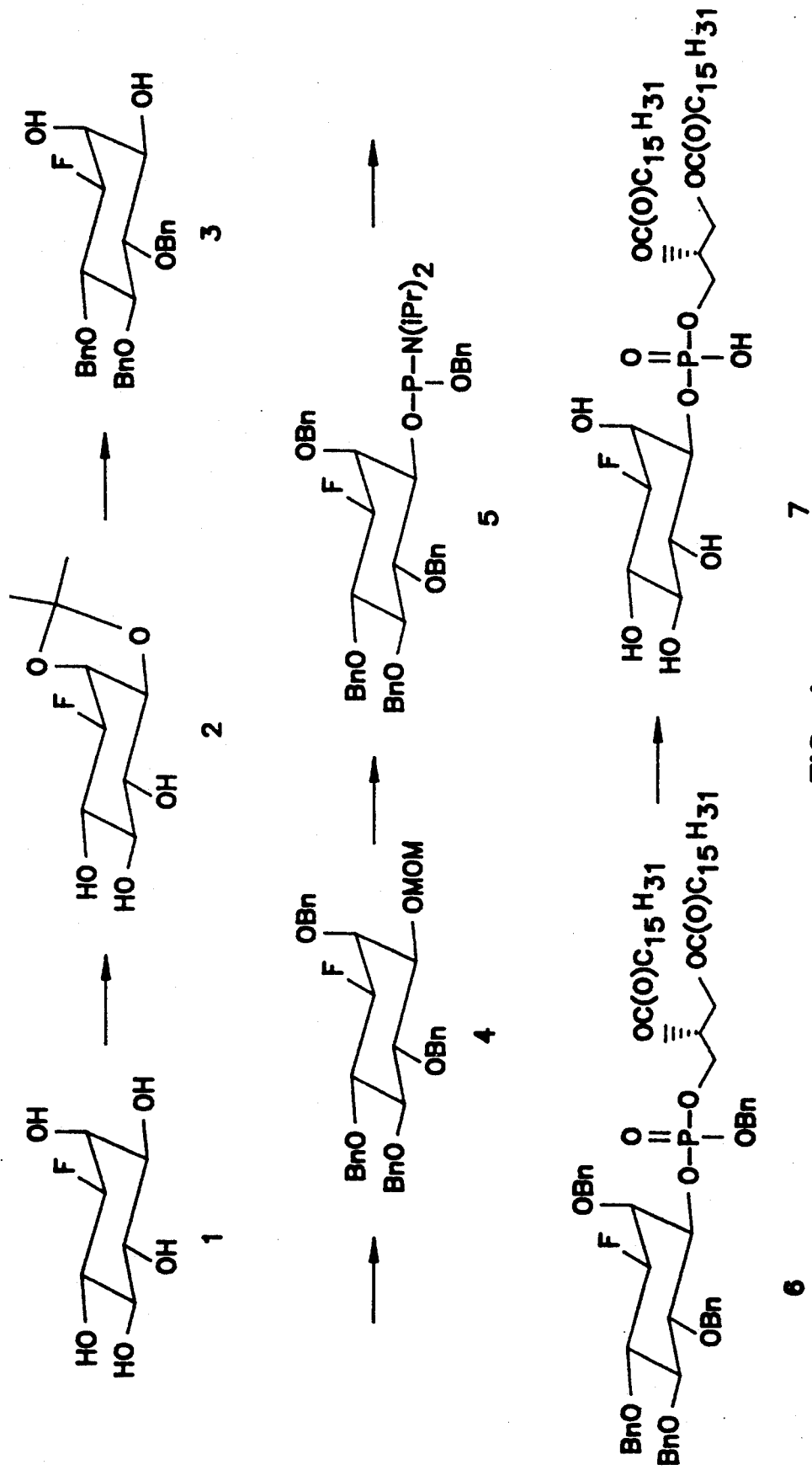
FIG. 1 is a schematic outline of the synthesis of 3-deoxy-3-fluoro-D-myo-inositol[(R)-2,3-bis(hexadecanoyloxy)propyl] hydrogen phosphate (7).
Figure 2:
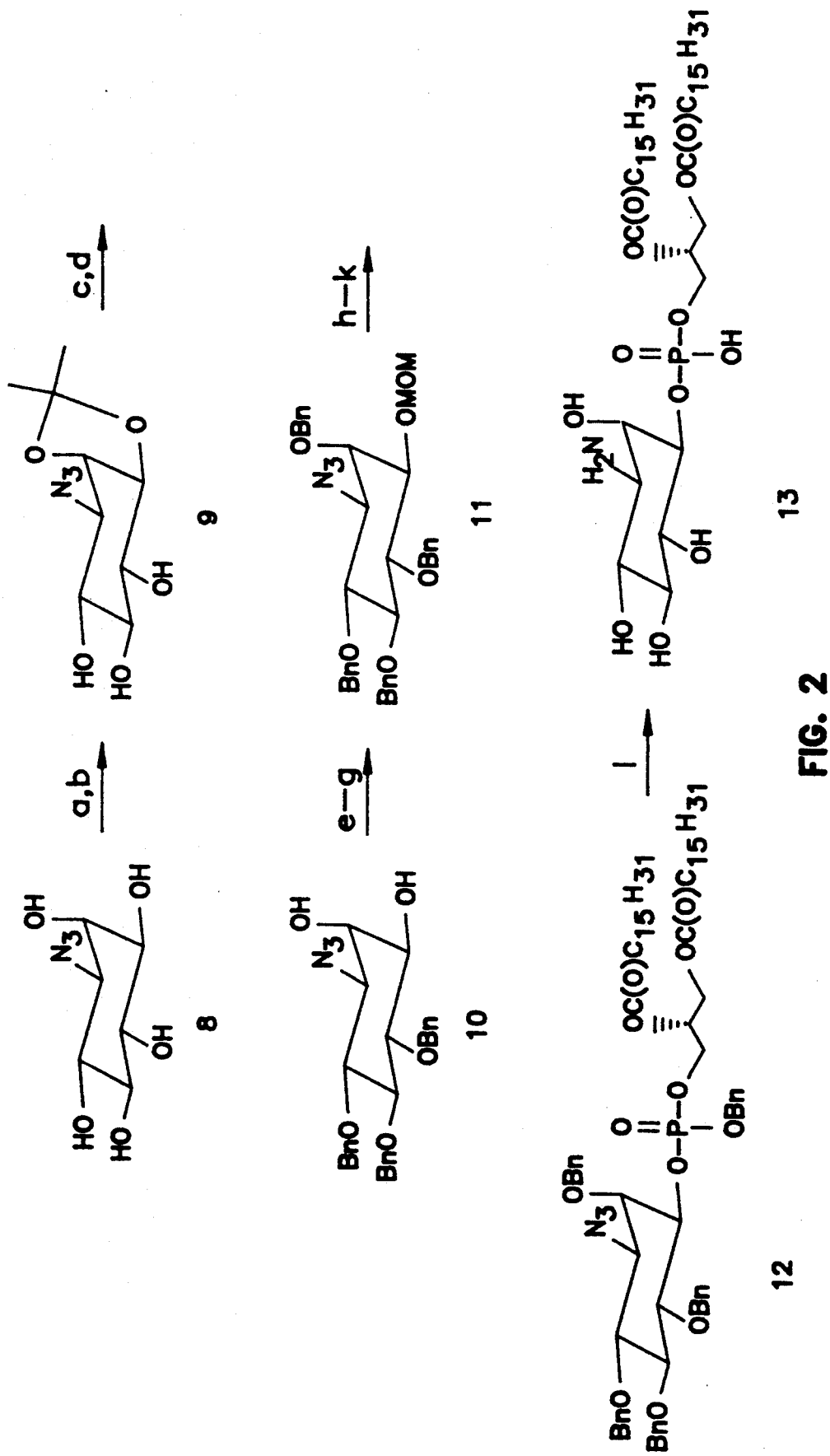
FIG. 2 is a schematic outline of the synthesis of 3-amino-3-deoxy-D-myo-inositol[(R)-2,3-bis(hexadecanoyloxy)propyl] hydrogen phosphate (13).
Figure 3:
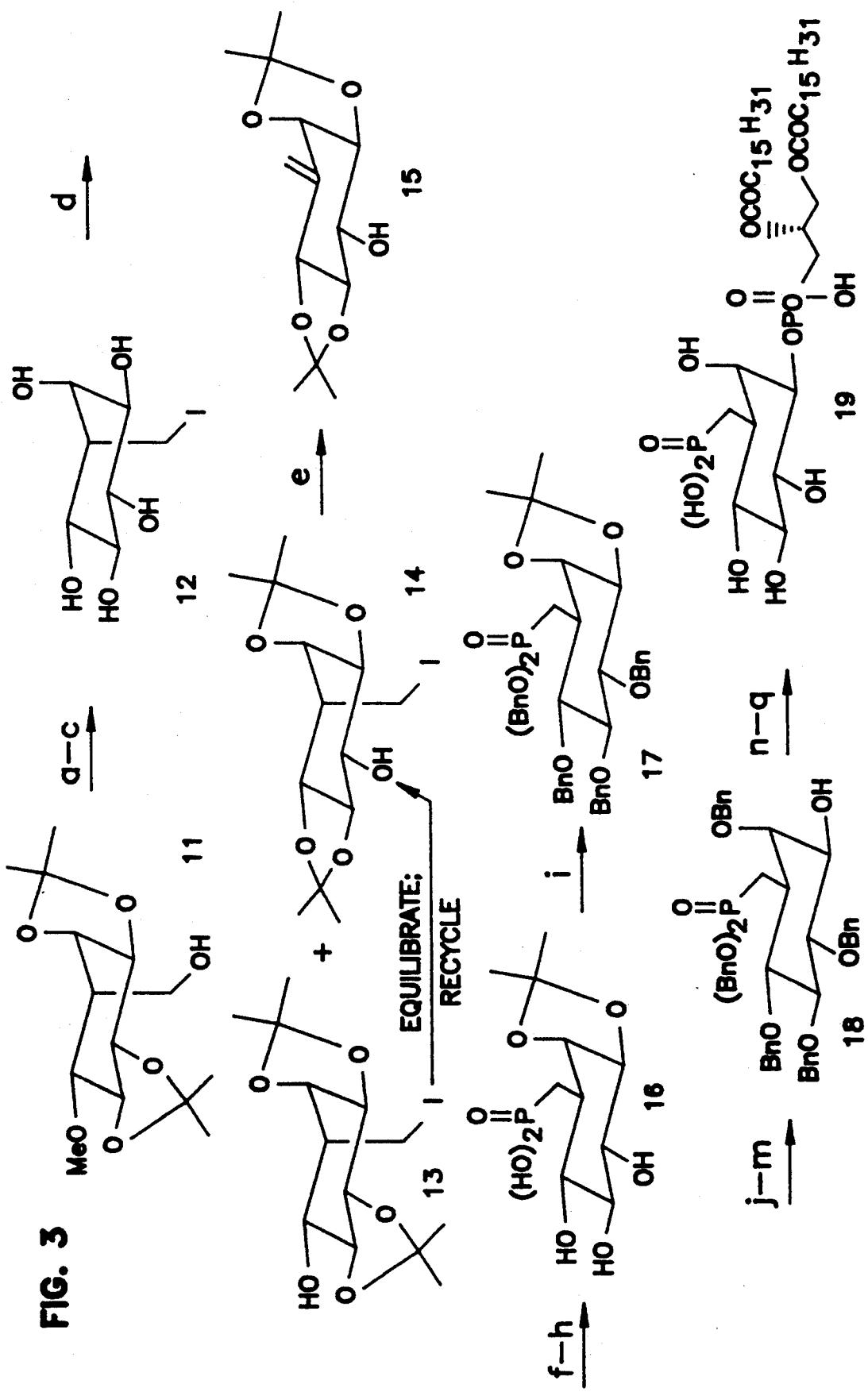
FIG. 3 is a schematic outline of the synthesis of 3-deoxy-3-phosphonomethyl-D-myo-inositol[(R)-2,3-bis(hexadecanoyloxy)propyl] hydrogen phosphate (19).

The phosphatidylinositol analogs of formula I (Y=O) are generally prepared starting with the corresponding 3-deoxy-3-substituted-myo-inositol, such as 3-deoxy-3-fluoro-myo-inositol depicted as compound 1 in FIG. 1, or 3-deoxy-3-azido inositol depicted as compound 8 in FIG. 2. Using selective protection/deprotection reactions known to the art, a corresponding protected 3-deoxy-3-substituted myo-inositol is obtained, wherein the 1-hydroxyl group is protected with a group, such as the methoxymethyl moiety shown for compound 4 in FIG. 1 (or compound 11 in FIG. 2), which can be removed while retaining the benzyl protecting groups on the remaining OH groups. The protecting group is then selectively removed from the 1-OH group, i.e., with aqueous acid, and the free 1-OH group is phosphitylated to yield the 1-(O-benzyl-N,N-diisopropyl)phosphoramidite, i.e., compound 5 in FIG. 1. This compound can be converted into the pentakis-protected (1,2-dialkanoyl-3-propyl)phosphate by reaction of the phosphoramidite with 1,2-dialkanoyl-glycerol and tetrazole in an organic solvent, followed by oxidation of the protected phosphite to the phosphate with a peroxide, i.e., to yield compound 6 in FIG. 1. Removal of the five protecting groups (benzyl in compound 6) yields the 3-deoxy-3-substituted-myo-inositol phosphatidyl compound of formula I.

Figure 4:
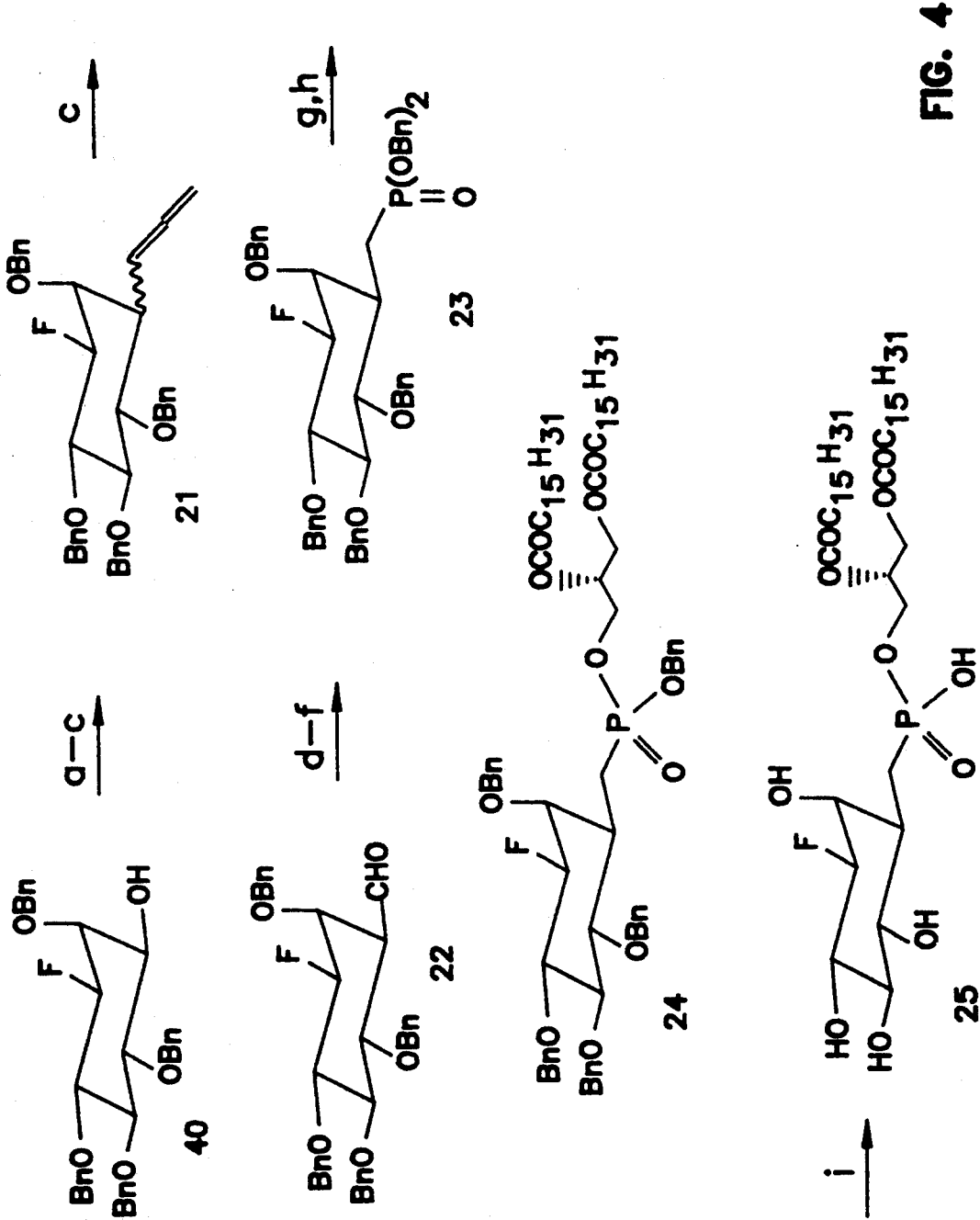
FIG. 4 is a schematic outline of the synthesis of 1-(O-[(R)-2,3-bis(hexadecanoyloxy)propyl]phosphonomethyl)-1,3-dideoxy-3-fluoro-D-myo-inositol (25).

The phosphatidyl inositol analogs of formula I (Y=CH₂) are generally prepared from the 2,4,5,6-tetrakisprotected 3-deoxy-3-substituted myo-inositols, such as 2,4,5,6-tetra-O-benzyl-3-deoxy-3-fluoro-myo-inositol shown as compound 40 in FIG. 4. The inositol-1-OH group of 40 is converted to the moiety —CH₂-P(O)(OBn)₂ (Bn=benzyl) by the steps outlined for the conversion of 40 to 23 on Table I, below. The bis-protected phosphonate is mono-deprotected and coupled to a 1,2-dialkanoylglycerol moiety using the conditions for the conversion of 23 to 24 (Table I). Removal of the five benzyl protecting groups by hydrogenolysis yields the 1-[O-(alkylphosphonyl)methyl-D-myo-inositol, i.e., 25 on FIG. 4.

TABLE I

| Synthesis of Compound 25 | | |
|---|---|---|
| Starting Material | Reagents | Product |
| 40 | a) NaH; CS₂; MeI | 21 |

TABLE I-continued

| Synthesis of Compound 25 | | |
|---|---|---|
| Starting Material | Reagents | Product |
| | b) HC≡C—CH₂SnBu₃ AIBN | |
| 21 | Ozone, Me₂S; separate axial and equatorial isomers; equilibrate axial isomer with DBU | 22 |
| 22 | a) NaBH₄ b) I₂, PPh₃, imidazole c) NaP(O) (OBn)₂ | 23 |
| 23 | a) 1 eq. 2-mercaptobenzothiazole, i-Pr₂NEt b) 1,2-dipalmitoyl-sn-glycerol, mesitylene-sulfonyl chloride | 24 |
| 24 | H₂, Pd(OH)₂/C, t-BuOH | 25 |

Figure 5:
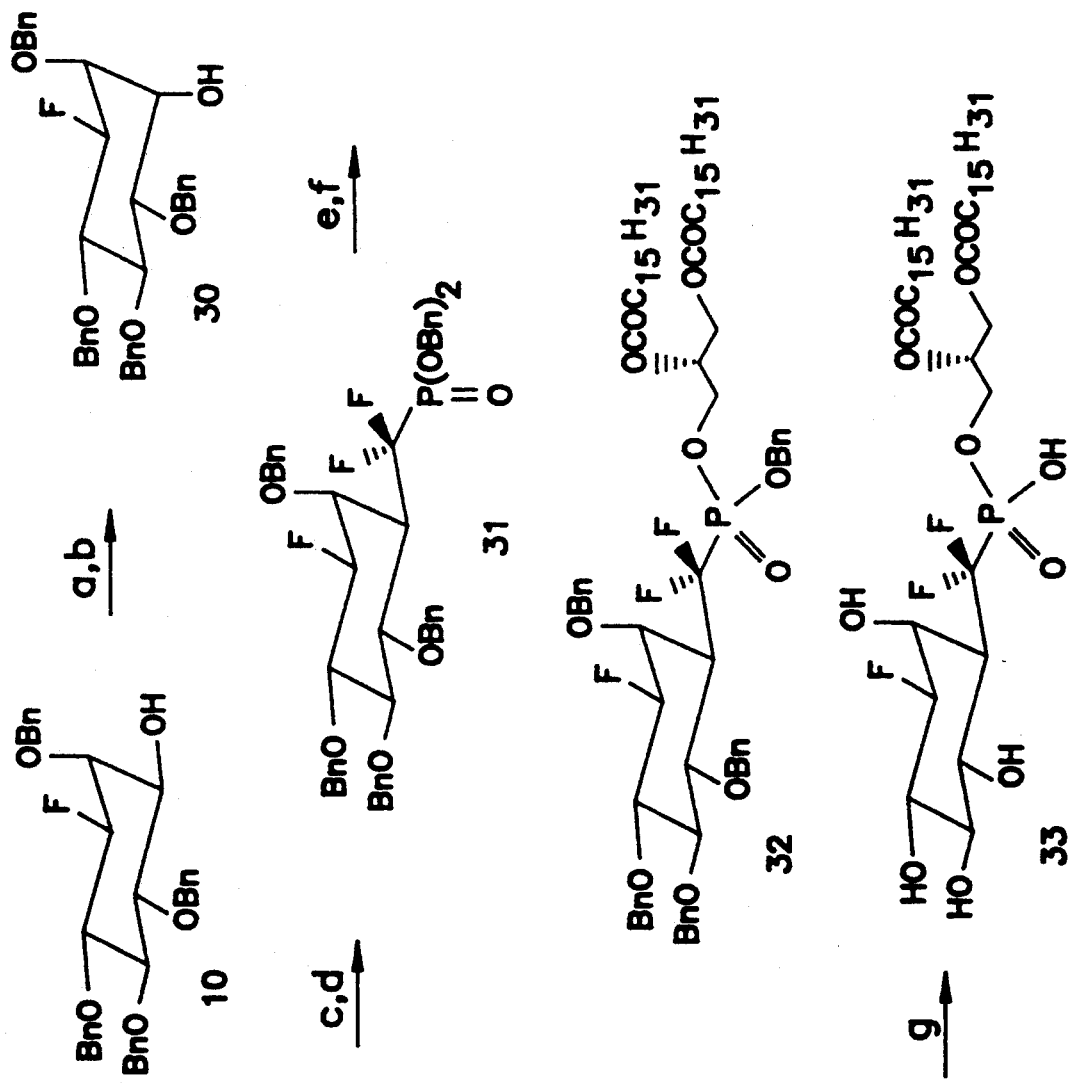
FIG. 5 is a schematic depiction of the synthesis of 1-[[O-[(R)-2,3-bis(hexadecanoyloxy)propyl]phosphono]difluoromethyl]-1,3-dideoxy-3-fluoro-D-myo-inositol (33).

The phosphatidylinositol analogs of formula I (Y=CF₂) can also generally be prepared starting with a 2,4,5,6-tetrakis-protected 3-deoxy-3-substituted myo-inositol, such as compound 10 as shown on FIG. 5. The stereochemistry of the 1-OH group is inverted by sequential oxidation, followed by stereoselective reduction of the 1-keto moiety with a selective reducing agent such as L-Selectride ® (Aldrich), LS-Selectride ® and the like, to yield an inositol of a configuration corresponding to that of compound 30 (FIG. 5). The axial 1-OH group is then derivatized with a suitable leaving group, such as triflate, and the 1-(CF₂-P(O)(OBn)₂) group is introduced by reaction of the triflate with the organozinc reagent derived from dibenzyl bromodifluoromethylphosphonate and zinc metal, catalyzed by CuI. The moiety CF₂P(O)(OBn)₂ is then converted into the substituent (CF₂P(O)(OH)—O—CH₂—CH(OR¹-)—CHOR²)); and the OH protecting groups are removed to yield the final product, e.g., 33, by the reaction sequence corresponding to that used to convert compound 23 to compound 25 (Table I).

The syntheses of a wide variety of 3-deoxy-3-substituted-myo-inositols, or of hydroxyl-protected 3-deoxy-3-substituted myo-inositols which are useful as starting materials in the preparation of the compounds of formula I, have been reported. For example, A. P. Kozikowski (U.S. Pat. Nos. 4,988,682 and 5,033,399) discloses the synthesis of 3-deoxy-3-fluoro-myo-inositol from quebrachitol; as well as the synthesis of 3-deoxy-3-mercapto-myo-inositol and 3-cyano-3-deoxy-myo-inositol. S. S. Yang (U.S. Pat. No. 4,515,722) discloses the synthesis of 3-azido-3-deoxy-1,2:4, 5-dicyclohexylidene-myo-inositol. The synthesis of 3-azido-3-deoxy-myo-inositol has been described by A. P. Kozikowski et al., *Cancer Chemother. Pharmacol.*, 29, 95 (1991).

Conversion of 3-deoxy-3-substituted phosphatidylinositols such as the 3-amino-, 3-mercapto-, 3-fluoro- or 3-cyano-substituted compounds to 3-substituted compounds of formula I wherein X is N(R)₂, SR, OR, chloro, bromo, iodo, CO₂R, —NC and the like is readily accomplished by conventional methodology, for example, when the phosphatidylinositol or a precursor thereof is in the fully protected form, e.g., compounds 4, 5 or 6 in FIG. 1. For example, phenyl- or alkylthio- derivatives can be prepared from the corresponding thiols by the procedure of U.S. Pat. No. 4,383,114 (Ex. 6). Pharmaceutically acceptable salts of the compound of formula I can also be prepared as described in U.S. Pat. No. 4,383,114.

Mode of Administration and Pharmaceutical Compositions

When the compounds of formula I are utilized in vivo, such compounds can be administered orally, topically, parenterally, by inhalation spray or rectally in dosage unit formulations containing conventional non-toxic pharmaceutically acceptable carriers.

Accordingly, the present invention also provides pharmaceutical compositions, including pharmaceutical unit dosage forms, comprising the compounds of formula I in combination with a pharmaceutically acceptable carrier. Useful pharmaceutically acceptable carriers include solid or liquid diluents, ingestible capsules or microcapsules, and inert matrices, such as latexes, pseudolatexes and hydrogels, for the controlled release of the compounds of formula I.

The term parenteral as used herein includes subcutaneous injections, intravenous, intramuscular, intrasternal injection or infusion techniques. In addition to the treatment of mammals, such as mice, rats, horses, dogs, cats, etc., the compounds of the invention are effective in the treatment of humans.

The pharmaceutical compositions containing the active ingredient may be in unit dosage forms suitable for oral ingestion, for example, as tablets, troches, lozenges, aqueous or oily suspensions, dispersible powders or granules, emulsions, hard or soft gelatin capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation.

Unit dosage forms for oral ingestion include tablets which contain the active ingredient in admixture with non-toxic pharmaceutically acceptable excipients. These excipients may be, for example, inert diluents, such as calcium carbonate, sodium carbonate, lactose, calcium phosphate or sodium phosphate, granulating and disintegrating agents, for example, maize starch, or alginic acid; binding agents, for example, starch, gelatin or acacia, and lubricating agents, for example, magnesium stearate, stearic acid or talc. The tables may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Unit dosage forms for oral ingestion may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, polyoxyalkylene glycols, peanut oil, liquid paraffin, or olive oil.

Aqueous suspensions usually contain the compound of formula I in admixture with appropriate excipients. Such excipients are suspending agents, for example, sodium carboxymethylcellulose, methylcellulose, hydroxypropylmethylcellulose, sodium alginate, polyvinylpryrolidone, gum tragacanth and gum acacia; non-toxic dispersing or wetting agents which may be a naturally occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ethyl, n-propyl, or p-hydroxybenzoates; one or more coloring agents; one or more flavoring agents; and one or more sweetening agents such as sucrose, Nutrasweet ®, or saccharin.

Oil suspensions may be formulated by suspending the compound of formula I in a vegetable oil, for example, arachis oil, olive oil, sesame oil or coconut oil, or in a mineral oil such as liquid paraffin. The oily suspension may contain a thickening agent, for example, beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the compound of formula I in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally occurring gums, for example, gum acacia or gum tragacanth, naturally occurring phosphatides, for example, soybean lecithin; and esters including partial esters derived from fatty acids and hexitol anhydrides, for example, sorbitan mono-oleate, and condensation products of said partial esters with ethylene oxide, for example, polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable aqueous or oleageous suspension. This suspension may be formulated according to the known art using those suitable dispersing or wetting agents and suspending agents which have been disclosed above. The sterile injectable preparation may be a sterile injectable solution or suspension in a non-toxic parenterally acceptable diluent or solvent. Among the acceptable vehicles and solvents that may be employed are water, 1,3-butanediol, Ringer,s solution and isotonic sodium chloride solution. In addition, sterile fixed oils are conventionally employed as a solvent or suspending medium. For this purpose any bland fixed oil may be employed including synthetic mono- or diglycerides. Fatty acids such as oleic acid also find use in the preparation of injectables.

The compounds of formula I can also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt to release the drug, for example, cocoa butter and polyethylene glycols.

When the compounds of formula I are utilized in vivo, dosage levels on the order of from about 0.2 mg to about 300 mg, preferably from about 10 mg to about 100 mg, per kilogram of body weight per day are useful.

The amount of active ingredient that may be combined with the carrier materials to produce a single dosage form will vary depending upon the host treated and the particular mode of administration. For example, a formulation intended for the oral administration of humans may contain from 5 mg to 5 g of active agent compounded with an appropriate and convenient amount of carrier material which may vary from about 5 to about 95 percent of the total composition. Pharmaceutical unit dosage forms will generally contain between from about 25 mg to about 500 mg of active ingredient.

The present invention also provides an article of manufacture comprising packaging material, such as an ampoule, vial, bottle, intravenous bag, and the like, and at least one compound of formula I contained therein. Preferably contained therein is at least one pharmaceutical unit dosage form comprising an amount of a compound of formula I in combination with at least one pharmaceutically acceptable carrier, as described above. Said packaging material further comprises a label or other associated instructional material such as a paper package insert or a sound recording, which indicates that said compound of formula I can be (a) used to treat a neoplastic condition, such as a particular carcinoma or cell proliferation disorder, or (b) used as an anti-inflammatory or analgesic agent.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The invention will be further described by reference to the following detailed examples, wherein tetrahydrofuran (THF) was dried over sodium/benzophenone. Dimethylformamide (DMF) was distilled in an aspirator vacuum over $CaH_2$. Methylene chloride was distilled over phosphorus pentoxide, and for use in phosphoramidite coupling, redistilled over $CaH_2$. Acetonitrile was distilled over phosphorus pentoxide and redistilled over calcium hydride. Methanol was refluxed for several hours over magnesium turnings, then distilled. Toluene and triethylamine were distilled over calcium hydride. Ethyl acetate and hexane were distilled, other solvents not referred to as "dry" were used as received. Commercial grade tetrazole was purified by vacuum sublimation as described by M. H. Caruthers et al., *Methods Enzymol.*, 154, 287 (1987). (Caution, explosion hazard!). Diisopropylammonium tetrazolide and O-benzyl-N,N,N',N'-tetraisopropylphosphorodiamidite were prepared as disclosed by Caruthers et al., *ibid.*, and by W. Bannwarth et al., *Helv. Chim. Acta*, 70, 175 (1987). Other reagents were commercially available and were used as received. Column chromatography was performed on EM Science No. 7734-7 silica gel 60, particle size 0.063–0.200 mm, thin layer chromatography on EM Science No. 5715 silica gel 60 $F_{254}$ glass plates, layer thickness 0.25 mm. TLC spots were visualized with permanganate solution. Melting points were measured in open capillaries and are uncorrected. NMR spectra were referenced to internal TMS ($^1H$), $CDCl_3$ or $DMSO-d_6$ ($^{13}C$, $\delta=77.09$ and 39.5), external $CFCl_3$ ($^{19}F$), and external 85% $H_3PO_4$ ($^{31}P$), respectively.

EXAMPLE 1

Preparation of 3-Deoxy-3-fluoro-D-myo-inositol [(R)-2,3-bis(hexadecanoyloxy)propyl] hydrogen phosphate (7)

A. Preparation of 3-Deoxy-3-fluoro-1, 2-O-isopropylidene-D-myo-inositol (2)

As summarized in FIG. 1, a solution of 3.54 g (19.4 mmol) of 3-deoxy-3-fluoro-D-myo-inositol, 7.6 ml (78 mmol) of 2-methoxypropene, and 100 mg of camphorsulfonic acid in 30 ml of dry DMF was stirred in a closed flask at 80° C. for 4 hr (Although little pressure buildup is observed, it is recommended to use safety shielding.). After cooling, 2 ml of triethylamine was added, and volatiles were evaporated in vacuo. The residue was taken up in methylene chloride, adsorbed on 20 g of silica gel, and chromatographed on silica gel with ethyl acetate/hexane 1:1 ($R_f$ approx. 0.6 and 0.4, resp.), to yield, after evaporation, 4.24 g (84%) of a mixture of diacetonides as a yellowish solid, of which the individual components have been previously separated and characterized as disclosed by A. P. Kozikowski et al., *J. Amer. Chem. Soc.*, 112, 7403 (1990). This material was dissolved in a mixture of 140 ml of dry methylene chloride and 70 ml of dry methanol, and 40 μl of acetyl chloride was added. The mixture was stirred under exclusion of moisture at 23° C. with close TLC monitoring (silica gel, methylene chloride/methanol 5:1; approximate $R_f$ values for fluorodeoxyinositol, the monoacetonide, and the diacetonide mixture are 0, 0.4, and 0.75, resp.). After 1 hr, most of the diacetonides had reacted while only a small amount of the completely deprotected inositol had been formed. The reaction was quenched by adding 0.5 ml of triethylamine, 30 g of silica gel was added, and the mixture was evaporated and chromatographed on silica gel with methylene chloride/methanol mixtures. With a 9:1 ratio of eluents, 0.38 g (9%) of the diacetonide mixture was recovered after which the ratio was changed to 5:1 to elute 2.89 g (80%) of compound 2 as a colourless semisolid of sufficient purity for the following step (Changing the eluent further to isopropanol/water 19:1 permitted the recovery of 0.24 g [8%] of fluorodeoxyinositol which, like the recovered diacetonide, could be recycled). The analytical sample was recrystallized from methanol/ethyl acetate: colorless needles, mp 147° C.; IR (nujol) 3397, 2922, 2853, 1374, 1227, 1156, 1105, 1034, 866 $cm^{-1}$; MS (EI) m/z 223 (M+H+), 207 (100%), 165, 129, 109, 73, 59; HRMS (M+—CH$_3$, $C_8H_{12}FO_5$) calcd 207.0669, found 207.0669; $[\alpha]^{23}_D -42.7°$, $[\alpha]^{23}_{578} -43.7°$ (c=6.9 gl$^{-1}$, methanol).

B 4,5,6-Tri-O-benzyl-3-deoxy-3-fluoro-1, 2-O-isopropylidene-D-myo-inositol

Under an argon atmosphere, 1.03 g (25.7 mmol) of NaH (60% dispersion in oil) was washed with dry THF and suspended in 10 ml of dry DMF. With ice cooling, 3.1 ml (26 mmol) of benzyl bromide was added dropwise, followed by a solution of 0.57 g (2.57 mmol) of compound 2 in 2.5 ml of dry DMF. The mixture was stirred at ice bath temperature for 3 hr, at 8°–10° C. for 3.5 hr, and at room temperature for another 3 hr. After recooling in an ice bath, 1 ml of water was added cautiously, and the mixture was directly filtered over silica gel (Larger runs require previous removal of the solvent.). Residual benzyl bromide was eluted with ethyl acetate/hexane 1:9, then the product was eluted with ethyl acetate/hexane 1:6. Evaporation and drying in vacuo left 1.21 g (96%) of the tribenzyl ether as a colorless oil: IR (neat film) 3033, 2986, 2932, 1497, 1455, 1372, 1215, 1073, 866, 737, 696 cm$^{-1}$; MS (EI) m/z 477 (M$^+$—CH$_3$), 401, 295, 91 (100%); HRMS (M$^+$—CH$_3$, C$_{29}$H$_{30}$FO$_5$) calcd 477.2077, found 477.2077; $[\alpha]^{23}_D$ −11.7°; $[\alpha]^{23}_{578}$ −12.0° (c=9.6 gl$^{-1}$, CHCl$_3$).

C. 4,5,6-Tri-O-benzyl-3-deoxy-3-fluoro-D-myo-inositol (3)

A solution of 2.16 g (4.4 mmol) of the above intermediate of Ex. 1(B) in 100 ml of methanol was stirred with 5 drops of conc. HCl at room temperature for 21 hr. After addition of 1 ml of triethylamine, the solvent was evaporated. The residue was taken up in methylene chloride and adsorbed on 10 g of silica gel. Filtration over silica gel with ethyl acetate/hexane 2:3, evaporation, and drying in vacuo yields 1.98 g (100%) of compound 3 as a waxy colorless solid: mp 102°–104° C.; IR (neat film) 3386, 3031, 2926, 1497, 1455, 1358, 1150, 1129, 1059, 1021, 729, 696 cm$^{-1}$; MS (EI) m/z 361 (M$^+$—C$_7$H$_7$), 197, 107, 91 (100%); HRMS (M$^+$—C$_7$H$_7$, C$_{20}$H$_{22}$FO$_5$) calcd 361.1451, found 361.1451; $[\alpha]^{23}_D$ −29.4°; $[\alpha]^{23}_{578}$ −30.8° (c=10.2 gl$^{-1}$, CHCl$_3$).

D. 4,5,6-Tri-O-benzyl-3-deoxy-3-fluoro-1-O-(methoxymethyl)-D-myo-inositol

A solution of 1.05 g (2.32 mmol) of 3 in 80 ml of dry methanol was refluxed under argon with 575 mg (2.31 mmol) of di-n-butyltin oxide for 2 hr to yield a clear solution. The cooled solution was evaporated to dryness and evaporated twice more with 10 ml of toluene each time. The residue was taken up in 10 ml of dry DMF and cooled under argon with an external ice bath. A solution of 193 μl (2.54 mmol) of chloromethyl methyl ether in 5 ml of dry toluene was added over a period of 50 min. Stirring in the ice bath was continued for 1 hr, then 200 ml of water was added, and the product was extracted into 3×50 ml of methylene chloride. After drying over MgSO$_4$, 10 g of silica gel was added, and the solvent was evaporated. The residue was chromatographed on silica gel with ethyl acetate/hexane mixtures, changing the composition from 1:3 (to elute a forerun) to 1:2 for the product, finally to 1:1 for unreacted started material. The respective solutions, after evaporation and drying in vacuo, yielded 139 mg (13%) of starting material 3 and 867 mg (75%) of the title compound. The analytical sample was obtained from methylene chloride/hexane as cotton-like needles: mp 118°–119° C.; IR (neat film) 3476, 3029, 2909, 1453, 1356, 1152, 1090, 1040, 899, 735, 695 cm$^{-1}$; MS (EI) m/z 451 (M$^+$—CH$_2$OCH$_3$), 405 (M$^+$—C$_7$H$_7$) 373, 91 (100%); $[\alpha]^{23}_D$ +37.7°, $[\alpha]^{23}_{578}$ +39.9° (c=11.4 gl$^{-1}$, CHCl$_3$).

E. 2,4,5,6-Tetra-O-benzyl-3-deoxy-3-fluoro-1-O-(methoxymethyl)-D-myo-inositol (4)

Under an argon atmosphere, 94 mg (2.35 mmol) of sodium hydride was washed with dry THF. A solution of 584 mg (1.18 mmol) of the above intermediate in 5 ml of dry DMF was added dropwise with water cooling, followed by 0.42 ml (3.5 mmol) of benzyl bromide. After stirring in the water bath for 5 hr, 5 drops of water were added, and the mixture was directly chromatographed on silica gel with ethyl acetate/hexane mixtures (1:7 for the forerun, 1:4 for the product). Evaporation and drying in vacuo left 680 mg (98%) of 4 as a colorless oil: IR (neat film) 3031, 2928, 1497, 1455, 1358, 1090, 1036, 916, 735, 696 cm$^{-1}$; MS (EI) m/z 541 (M$^{30}$—CH$_2$OCH$_3$), 495 (M$^{30}$—C$_7$H$_7$) 463, 181, 91 (100%); HRMS (M$^+$—C$_7$H$_7$, C$_{29}$H$_{32}$FO$_6$) calcd 495.2183, found 495.2183; $[\alpha]^{23}_D$ +16.1°; $[\alpha]^{23}_{578}$ +16.3° (c=8.1 gl$^{-1}$, CHCl$_3$).

F. 2,4,5,6-Tetra-O-benzyl-3-deoxy-3-fluoro-D-myo-inositol (40)

A solution of 874 mg (1.49 mmol) of 4 in 30 ml of methanol, 3 ml of water, and 0.3 ml of concentrated HCl was heated under reflux for 5 hr. After cooling, the mixture was evaporated, and the residue was chromatographed on silica gel with ethyl acetate 1:6 (forerun), then 1:3 (product) to leave, after evaporation and drying in vacuo, 57 mg (94%) of a colorless solid: mp 49°–50.5° C.; $^{13}$C NMR (CDCl$_3$) δ 138.30, 138.20, 138.11, 128.47, 128.34, 128.05, 127.99, 127.82, 127.72, 127.63, 93.74 (d, J=187.5 Hz), 82.11 (d, J=14 Hz), 81.66, 80.38 (d, J=17 Hz), 77.83 (d, J=16.5 Hz) 75.80, 75.52, 75.36, 74.96, 71.00 (d, J=11.5 Hz); IR (neat film) 3451, 3033, 1455, 1360, 1069, 737, 698 cm$^{-1}$; MS (EI) m/z 451 (M$^+$—C$_7$H$_7$), 181, 91 (100%); $[\alpha]^{23}_D$ −19.9°, $[\alpha]^{23}_{578}$ −20.9° (c=9.3 gl$^{-1}$, CHCl$_3$).

G. 2,4,5,6-Tetra-O-benzyl-3-deoxy-3-fluoro-D-myo-inositol 1-(O-benzyl-N,N-diisopropyl) phosphoramidite (5)

Under an argon atmosphere and with water cooling, 36 mg (0.21 mmol) of diisopropylammonium tetrazolide was suspended in 1.5 ml of dry methylene chloride, and 0.18 ml (0.51 mmol) of O-benzyl-N,N, N',N'-tetraisopropylphosphorodiamidite was added dropwise within 10 min, followed by a solution of 228 mg (0.42 mmol) of alcohol 10 in 2.5 ml of dry methylene chloride. The mixture was stirred in the water bath for 20 hr, then 5 ml of saturated NaHCO$_3$ solution was added. The phases were separated, and the aqueous phase was extracted with 2×10 ml of methylene chloride. The combined organic phases were dried over Na$_2$SO$_4$ and evaporated, and the residue was rapidly filtered over 30 g of silica gel which had previously been deactivated by shaking with 0.5 ml of triethylamine, using ethyl acetate/hexane 1:4 as the eluent. Evaporation and drying in vacuo afforded 318 mg (97%) of the phosphoramidite as a colorless syrup: IR (neat film) 3033, 2967, 2928, 1497, 1455, 1364, 1028, 801, 733, 696 cm$^{-1}$; MS (EI) m/z 628 (M$^+$—OC$_7$H$_7$—C$_3$H$_8$), 234, 219, 83 (100%): HRMS (M$^+$—OC$_7$H$_7$—C$_3$H$_8$, C$_{37}$H$_{40}$FNO$_5$P) calcd 628.2628, found 628.2628.

H.
2,4,5,6-Tetra-O-benzyl-3-deoxy-3-fluoro-D-myo-inositol 1-(benzyl)[(R)-2, 3-bis(hexadecanoyloxy)propyl]phosphite To 251 mg (441 μmol) of 1,2-dipalmitoyl-sn-glycerol and 58 mg (0.83 mmol) of tetrazole in 1.5 ml of dry methylene chloride was added at room temperature under argon a solution of 318 mg (408 μmol) of phosphoramidite 5 in 1.5 ml of dry acetonitrile. The resulting mixture was stirred for 5 hr at room temperature, then for 64 hr at 35°–40° C. After cooling, 10 ml of saturated $NaHCO_3$ solution was added, the phases were separated, and the aqueous phase was extracted with 3×20 ml of methylene chloride. The combined aqueous phases were dried over $Na_2SO_4$ and evaporated, and the residue was filtered over silica gel with ethyl acetate/hexane 1:8. Evaporation and drying in vacuo yielded 404 mg of the title compound (79% rel. to 5) of a colorless glass: IR (neat film) 3033, 2924, 2853, 1744, 1456, 1164, 1024, 735, 696 $cm^{-1}$; MS (EI) m/z 550, 451, 367, 91 (100%).

I.
2,4,5,6-Tetra-O-benzyl-3-deoxy-3-fluoro-D-myo-inositol 1-(benzyl)[(R)-2, 3-bis(hexadecanoyloxy)propyl]phosphate (6)

To an ice-cooled situation of 353 mg (283 μmol) of the above phosphite in 3 ml of dry methylene chloride under argon was added in 4 equal portions in 20 min intervals a total of 800 μl (400 μmol) of a 0.5 M solution of anhydrous tert-butyl hydroperoxide in methylene chloride. Stirring was continued in the ice bath for 90 min, then at room temperature for 20 min. The mixture was evaporated and filtered over silica gel with ethyl acetate/hexane 1:4 to obtain 351 mg (98%) of the phosphate 6 as a colorless syrup: IR (neat film) 2924, 2853, 1744, 1026, 696 $cm^{-1}$; MS (EI) m/z 550, 451, 367, 239, 91 (100%); (FAB) m/z 640, 551, 313, 181.

J.
3-Deoxy-3-fluoro-D-myo-inositol[(R)-2,3-bis(hexadecanoyloxy)propyl] hydrogen phosphate (7)

A solution of 54.2 mg (42.9 μmol) of 6 in 6 ml of tert-butanol was hydrogenated in a Parr shaker under 5 bar of hydrogen for 23.5 hr over 23.5 mg of 20% $Pd(OH)_2/C$ (Aldrich, containing 50% of water). The catalyst was removed by centrifugation and washed with tert-butanol, the solution was evaporated, and the residue was dried in vacuo to leave 27.9 mg (80%; variability of the yield over 6 runs: 71–89%) of phosphate 7 as a colorless amorphous solid: mp 132°–133° C. (after sintering); $^1H$ NMR ($CDCl_3/CD_3OD$ 2:1) δ 5.27 (m, 1 H, 2-H of glycerol), 4.45–4.35 (m, 2.5 H) 4.27–4.15 (m, 3.5 H), 4.02 (br, 1 H), 3.97 (dt, 1 H, J =9.5 Hz (t), 12 Hz (d)), 3.86 (br t, 1 H, J=8.5 Hz), 3.24 (t, 1 H, J=9.5 Hz), 2.36 (t, 2 H, J=7.5 Hz), 2.33 (t, 2 H, J=7.5 Hz) 1.62 (m, 4 H), 1.27 (m, 48 H), 0.89 (t, 6 H, J=7 Hz); $^{13}C$ NMR ($CDCl_3/CD_3$ OD 2:1) δ 173.67, 173.30, 91.30 (d, J=182.5 Hz), 73.46 (d, J=12.5 Hz), 70.82 (d, J=4 Hz), 70.42 (d, J=18 Hz), 69.52 (d, J=6 Hz); 69.08 (d, J=17.5 Hz), 64.85, 64.79, 61.86, 33.84, 33.73, 31.60, 29.34, 29.18, 29.00, 28.79, 24.53, 22.32, 13.57; $^{19}F$ NMR ($CDCl_3/CD_3OD$ 2:1) δ −204.51 (ddd, J=47, 11, 10 Hz); $^{31}P$ NMR ($CDCl_3/CD_3OD$ 2:1) δ −0.94 (br); IR (KBr) 3416, 2920, 2851, 1740, 1630, 1468, 1383, 1038 $cm^{-1}$; $[α]^{23}_D$ −1.3°, $[α]^{23}_{578}$ −1.3°, $[α]^{23}_{265}$ −4.2° (c=5.6 $gl^{-1}$, $CHCl_3/MeOH$ 2:1).

EXAMPLE 2
3-Amino-3-deoxy-D-myo-inositol[(R)-2, 3-bis(hexadecanoyloxy)propyl] hydrogen phosphate (13)

As depicted in FIG. 2, the synthesis of 13 starts from the 3-azido-3-deoxy-myo-inositol (8). The synthesis of 8 from L-quebrachitol has been described by A. P. Kozikowski et al., *Cancer Chemother. Pharmacol.* (in press). After a sequence of routine protection and deprotection steps, the MOM group was removed from intermediate 11, and the 1-position was then phosphitylated using O-benzyl-N,N,N',N'-tetraisopropylphosphorodiamidite. The coupling reaction with 1,2-dipalmitoyl-sn-glycerol was carried out and the phosphite intermediate oxidized to phosphate. Lastly, all of the benzyl groups were removed by hydrogenolysis in the presence of palladium hydroxide on carbon in t-butanol as solvent. Under these reaction conditions, the azido group was reduced to amine. The preparation of 3-azido-3-deoxyphosphatidylinositol can also be accomplished from 12. This requires an alternative method for debenzylation which can be accomplished by using trimethylsilyl iodide as the cleaving reagent.

More specifically, the conversion of 8 to 13 was accomplished as outlined on Table II, below.

TABLE II

| Starting Material | Reagents/Reaction Conditions | Product (yield) |
|---|---|---|
| 8 | (a) 2-methoxypropene, cat. camphorsulfonic acid 50° C., 18 hr; (b) $CH_3COCl$, $CH_2Cl_2$/MeOH (1:2), 25° C., 8 hr | 9 (71.3%) |
| 9 | (a) NaH, $PhCH_2Br$, DMF, 25° C. (b) conc. HCl, MeOH, 25° C., 12 hr | 10 (88%) |
| 10 | (a) $Bu_2SnO$, MeOH, reflux, 6 hr; (b) $MeOCH_2Cl$, $PhCH_3$, 0° C., 1 hr (c) NaH, $PhCH_2Br$, DMF, 25° C. | 11 (81%) |
| 11 | (a) conc. HCl, MeOH, $H_2O$; (b) $BnOP(Ni—Pr_2)_2$, diisopropylammonium tetrazolide, $CH_2Cl_2$, 25° C.; (c) 1,2-dipalmitoyl-sn-glycerol, tetrazole, $CH_2Cl_2/CH_3CN$ (1:1); (d) t-BuOOH, 0° C., 1.5 hr, 25° C., 3 hr | 12 (59%) |
| 12 | 5 atm $H_2$, 20% $Pd(OH)_2/C$, t-BuOH, 25° C., 1 day | 13 (70%) |

EXAMPLE 3
Synthesis of 3-Deoxy-3-phosphonomethyl-D-myo-inositol[(R)-2,3-bis(hexadecanoyloxy)propyl] hydrogen phosphate (19)

As outlined in FIG. 3, the synthesis starts from 11, readily available from quebrachitol by the procedure of H. Paulsen et al., *Liebige Ann. Chem.*, 1073 (1983). This compound has the incorrect stereochemistry at C-3 but is preferred as the starting material since it is more readily available than its epimer, and the C-3 stereochemistry will be lost in the later steps of the synthesis. Tosylation of the free hydroxyl group using TsCl and pyridine, followed by exchange of tosylate for iodide using NaI in acetone (or alternatively, shorter but in slightly lower yield, direct iodination of 11 using iodine, triphenylphosphine, and imidazole) yields the iodide which is deprotected by an excess of boron tribromide in methylene chloride. The resulting iodopentol (12) is reprotected as a regioisomeric mixture of diacetonides 13/14 by warming with 4 eq. of 2-methoxypropene in DMF under catalysis by camphorsulfonic acid. The isomer 13 can be transformed into 14 by resubjecting it to acid catalysis in warm DMF and recycling. Elimination of hydrogen iodide to obtain the olefin 15 is then brought about by treatment with DBU in THF at room temperature. The C=C double bond of 15 is cleaved to the ketone by ozonolysis followed by in situ reduction of the ozonide with dimethyl sulfide. The phosphonic acid side chain is installed by a Wadsworth-Emmons olefination using the sodium salt of tetrabenzyl methylenediphosphonate, followed by hydrogenation over palladium on carbon, which establishes the desired stereochemistry at C-3 and further removes the benzyl protecting groups of the phosphonate. Addition of water to the crude reaction mixture and stirring at room temperature cleaves the labile trans-acetonide due to the acidity of the phosphonate group. The crude triolphosphonic acid (16) which remains after filtration from the catalyst and evaporation is perbenzylated using excess sodium hydride and excess benzyl iodide in DMF to yield 17. The more nucleophilic alkoxide groups of 16 react before the phosphonate so that cyclic phosphonate formation which generally occurs when an alkoxide is adjacent to a phosphonate ester is largely avoided. The cis-acetonide protecting group of the resulting compound 17 is removed by acid treatment (MeOH,HCl) and the free equatorial 1-hydroxyl group temporarily protected as its methoxymethyl (MOM) derivative using $Bu_2SnO$ and methoxymethyl chloride. The less reactive axial hydroxyl group is now benzylated under acidic conditions using O-benzyltrichloroacetimidate and catalytic TfOH, and the MOM group is again removed by acidic hydrolysis to obtain the intermediate 18. The phosphatidic acid side chain is installed using the same technique as for 3-fluoro-3-deoxy-phosphatidylinositol (6), and finally catalytic hydrogenolysis ($H_2$, $Pd(OH)_2$, t—BuOH) yields the unprotected title compound 19.

EXAMPLE 4

Synthesis of 1-(O-[(R)-2,3-bis(hexadecanoyloxy)propyl]phosphonomethyl)-1,3-dideoxy-3-fluoro-D-myo-inositol (25)

To avoid problems resulting from the propensity of inosose intermediates for elimination, the side chain is instead introduced via a radical substitution reaction. As shown in FIG. 4, the starting material (40) is first derivatized to its methyl xanthate ester by reaction with $CS_2$ and NaH, which is subsequently transformed to a stereoisomeric mixture of allenes (21) with propargyltributylstannane under catalysis by azobis(isobutyronitrile). Ozonolysis with reductive workup ($Me_2S$) produces a mixture of aldehydes (22) which is separated by column chromatography; the minor axial isomer yields further equatorial product on treatment with DBU.

The equatorial aldehyde is reduced to the alcohol with sodium borohydride, and then transformed to the iodide ($I_2$, $PPh_3$, imidazole) which yields a protected phosphonate (23) on reaction with sodium dibenzylphosphite. One of the phosphonate benzyl groups is cleaved by treatment with a stoichiometric amount of 2-mercaptobenzotniazole and base, and the resulting monoanion is condensed with di-O-pal-mitoyl-sn-glycerol in the presence of mesitylenesulfonyl chloride, to yield 24. The title compound 25 is obtained by removal of the benzyl protective groups through catalytic hydrogenolysis ($H_2$, $Pd(OH)_2/C$, t—BuOH).

EXAMPLE 5

Synthesis of 1-[[O-[(R)-2,3-bis(hexadecanoyloxy)propyl]phosphono]difluoromethyl]1,3-dideoxy-3-fluoro-D-myo-inositol (33)

The key intermediate, 2,4,5,6-tetra-O-benzyl-3-deoxy-3-fluoro-D-myo-inositol (40), is available as outlined earlier. Inversion of the stereochemistry at C-1 is brought about by oxidation to the inosose (($COCl)_2$, DMSO, i-$Pr_2NEt$), followed by stereoselective reduction of the 1-ketone with L-Selectride® (Aldrich Chem. Co.). The resulting axial alcohol (30) is derivatized as its triflate ($Tf_2O$, $NEt_3$), and the phosphorus-containing side chain is introduced by the organozinc reagent derived from dibenzyl bromodifluoromethylphosphonate and zinc metal, catalyzed by cuprous iodide to yield 31. The further reaction sequence to yield 33 is the same as for compound 25.

EXAMPLE 6

Cell Growth Inhibition Studies

Wild type NIH 3T3 cells and v-sis oncogene-expressing NIH 3T3 cells were maintained in bulk culture in DMEM with 10% heat inactivated calf serum and passaged using 0.05% trypsin and 0.5 mM EDTA. For cell growth assays, the cells were plated at a density of $5 \times 10^3$ cells in 1.6 cm diameter culture wells in 0.5 ml DMEM containing 10% heat inactivated calf serum and allowed to attach to the surface of the well for 24 hr. The medium was then replaced with fresh medium containing the myo-inositol analogues. In studies where myo-inositol was omitted from the medium, myo-inositol-free DMEM and dialyzed, heat inactivated calf serum was used, which did not adversely affect cell growth over 3 days. Adherent cells were harvested after 3 days and were counted using an automated cell counter. Inhibition of cell growth caused by serial concentrations of analogues was expressed as a percentage of the number of nontreated cells at the end of the 3-day incubation period. Incubations were conducted in quadruplicate. The mean concentration of analogue required to cause 50% inhibition of cell growth ($IC_{50}$)±S.E. was calculated from nonlinear least-squares regression analysis of the cell-proliferation concentration data (P. L. Appel et al., Cancer Chemother. Pharmacol., 17, 47 (1986)).

The human colon carcinoma cell line, HT-29, was chosen as being representative of a clinically very important, slow growing and chemotherapy resistant human solid tumor. Many human colon cancer lines, including HT-29, have the v-sis oncogene (D. L. Trainer et al., Int. J. Cancer, 41, 287 (1988)). The growth of HT-29 cells was measured by colony formation in the soft agar colony forming assay over 7 days, with automated colony counting using a Omicon 3600 Image Analysis System, as described previously by M. C. Alley et al., 44, 549 (1984).

All soft-agarose cultures were performed in similar fashion. Each 35-mm culture dish contained a base layer consisting of 0.5 ml of standard DMEM culture medium (with 40 μM myo-inositol) with 0.5% agarose. On Day 0, cells in bulk culture were dissociated with trypsin and EDTA, washed once in growth medium, and subcultured by layering $1 \times 10^4$ viable cells in 0.5 ml of growth medium with 0.3% agarose over each base layer. Cultures were maintained in cell culture incubators at 37° C., 5% $CO_2$:95% air, and 100% relative humidity. On Day 1 (24 hr later), an upper layer of 1 ml of growth medium containing drug was applied to each culture. Cell lines formed a sufficient number of detectable colonies (>60 μm diameter) for analysis following 7 days of incubation. Viable colonies were stained using a metabolizable tetrazolium salt, 2-(p-iodophenyl)-3-(p-nitrophenyl)-5-phenyltetrazolium chloride.

The growth inhibitory effects of D-3-deoxy-3-fluoro-phosphatidylinositol (7) compared with those of D-3-deoxy-fluoro-myo-inositol are shown in Table 3. The results show the following. First, compound 7 is a more potent inhibitor of cell growth than the simple myo-inositol analogue (up to 1,000 fold with wild type NIH 3T3 cells). Second, growth inhibition by compound 7 is not antagonized by myo-inositol at physiological concentrations. Third, selectivity for growth inhibition of v-sis compared to wild type NIH 3T3 cell is lost.

TABLE 3

Cell growth inhibition by 3-deoxy-3-fluoro-myo-inositol and 3-deoxy-fluoro-phosphatidylinositol (7)

| | NIH $IC_{50}$ (μM) | v-sis NIH $IC_{50}$ (μM) |
|---|---|---|
| 3-deoxy-3-fluoro-myo-inositol | | |
| − myo-inositol | 7,000 ± 130 | 1,000 ± 600 |
| + myo-inositol | $NT^a$ | NT |
| 3-deoxy-3-fluoro-phosphatidylinositol (7) | | |
| − myo-inositol | 110 ± 20 | 107 ± 15 |
| + myo-inositol | 99 ± 13 | 81 ± 11 |

$^a$NT = nontoxic. $IC_{50}$ > 33 mM. Values are ± S.E. of mean.

Figure 6:
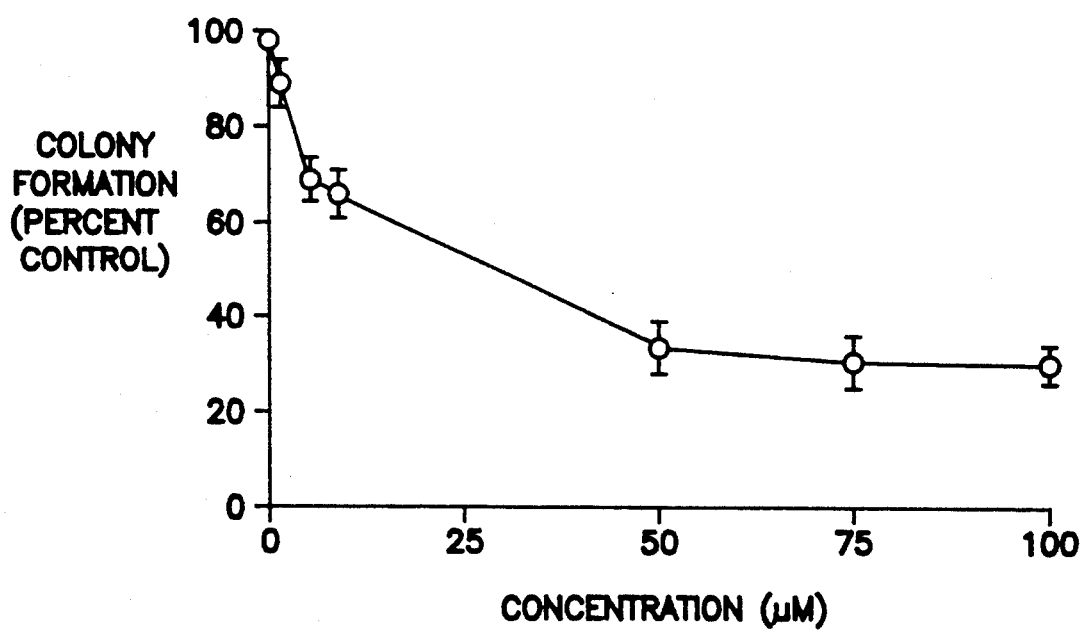

Inhibition of colony formation of HT-29 human colon carcinoma cells by D-3-deoxy-3-fluoro-phosphatidylinositol (7) is shown in FIG. 6. The calculated $IC_{50}$ for inhibition of colony formation was 53±9 μM.

All cited patents and publications are incorporated by reference herein. The invention has been described with reference to various specific and preferred embodiments and techniques. However, it should be understood that many variations and modifications may be made while remaining within the spirit and scope of the invention.

What is claimed is:

1. A 3-deoxy-3-substituted analog of phosphatidyl inositol of formula:

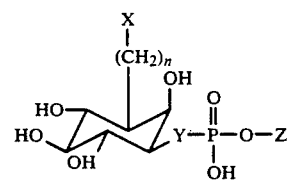

or a pharmaceutically acceptable salt thereof, wherein X is selected from the group consisting of halo, $N_3$, CN, —NC, OR, SR, $N(R)_2$, $CO_2R$, C(O)R, $P(O)(OR)_2$, $CF_3$, S(O)R and $SO_2R$; wherein each R is H, $(C_1-C_{22})$alkyl, $(C_6-C_{10})$aryl, $(C_3-C_8)$-cycloalkyl, $(C_2-C_{22})$alkenyl, $(C_5-C_8)$cycloalkenyl, $(C_7-C_{32})$-aralkyl, $(C_7-C_{32})$alkylaryl, $(C_9-C_{32})$aralkenyl or $(C_9-C_{32})$-alkenylaryl; n is 0 or 1, with the proviso that when n is 0, X is not OH, Y is O, S, NR, $CH_2$, $CF_2$ or CHF; and Z is

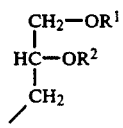

wherein $R^1$ and $R^2$ are individually R, —C(O)R, —$CO_2R$, —C(O)NHR, C(O)SR or $P(O)(OR)_2$.

2. The compound of claim 1 wherein Y is O, $CH_2$ or $CF_2$.

3. The compound of claims 1 or 2 wherein n is 0.

4. The compound of claims 1 or 2 wherein $R^1$ and $R^2$ are individually $(C_1-C_{22})$alkyl, $(C_{12}-C_{22})$ alkanoyl or $(C_{12}-C_{22})$alkenoyl.

5. The compound of claim 3 wherein X is halo.

6. The compound of claim 5 wherein X is F.

7. The compound of claim 3 wherein X amino.

8. The compound of claim 3 wherein X is $N_3$.

9. The compound of claim 4 wherein X is $P(O)(OR)_2$ and n is 1.

10. The compound of claim 9 wherein R is H.

11. 3-amino-3-deoxy-D-myo-inositol[(R)-2,3-bis(hexadecanoyloxy)propyl] hydrogen phosphate.

12. 3-deoxy-3-fluoro-D-myo-inositol[(R)-2,3-bis(hexadecanoyloxy)propyl] hydrogen phosphate.

13. 3-deoxy-3-phosphonomethyl-D-myo-inositol[(R)-2,3-bis(hexadecanoyloxy)propyl] hydrogen phosphate.

14. 1-(O-[(R)-2,3-bis(hexadecanoyloxy)propyl]phosphonomethyl)-1,3-dideoxy-3-fluoro-D-myo-inositol.

15. 1-[[O-[(R)-2,3-bis(hexadecanoyloxy)propyl]phosphonyl]difluoromethyl]-1,3-dideoxy-3-fluoro-D-myo-inositol.

* * * * *

UNITED STATES PATENT AND TRADEMARK OFFICE
CERTIFICATE OF CORRECTION

PATENT NO. : 5,227,508

DATED : July 13, 1993

INVENTOR(S) : Alan P. Kozikowski, et al

It is certified that error appears in the above-indentified patent and that said Letters Patent is hereby corrected as shown below:

Column 2, line 20, "Biochim." should read --Biochem.--.

Column 6 line 22, "on" should read --in--.

Column 7, line 46, "tables" should read --tablets--.

Column 9, line 66, "Chim" should read --Chem.--.

Column 12, line 18, "$M^{30}$" should read --$M^+$-- in both instances.

Column 12, line 32, "57" should read --757--.

UNITED STATES PATENT AND TRADEMARK OFFICE
CERTIFICATE OF CORRECTION

PATENT NO. : 5,227,508
DATED : July 13, 1993
INVENTOR(S) : Alan P. Kozikowski, et al It is certified that error appears in the above-indentified patent and that said Letters Patent is hereby corrected as shown below:

Column 12, line 44, "(0-benzvl" should read --(0-benzyl--.

Column 13, line 67, "$\alpha^{23}$ 265" should read --$\alpha^{23}$ 365--.

Column 15, line 65, "mercaptobenzotniazole" should read --mercaptobenzothiazole--.

Column 18, line 37, insert --is-- after the letter "X".

Signed and Sealed this

Twenty-fourth Day of May, 1994

Attest:

BRUCE LEHMAN

Attesting Officer   Commissioner of Patents and Trademarks